(12) United States Patent
Scirica

(10) Patent No.: US 10,070,865 B2
(45) Date of Patent: Sep. 11, 2018

(54) TRAVEL CLIP FOR SURGICAL STAPLE CARTRIDGE

(71) Applicant: Covidien LP, Mansfield, MA (US)

(72) Inventor: Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 453 days.

(21) Appl. No.: 14/816,303

(22) Filed: Aug. 3, 2015

(65) Prior Publication Data

US 2015/0335330 A1    Nov. 26, 2015

Related U.S. Application Data

(62) Division of application No. 13/422,320, filed on Mar. 16, 2012, now Pat. No. 9,113,881.

(51) Int. Cl.
| | |
|---|---|
| *A61B 17/10* | (2006.01) |
| *A61B 17/068* | (2006.01) |
| *A61B 17/072* | (2006.01) |
| *A61B 90/92* | (2016.01) |

(52) U.S. Cl.
CPC .......... *A61B 17/105* (2013.01); *A61B 17/068* (2013.01); *A61B 17/07207* (2013.01); *A61B 90/92* (2016.02); *A61B 2017/0688* (2013.01); *A61B 2017/07271* (2013.01)

(58) Field of Classification Search
CPC ............ A61B 50/30; A61B 2090/0801; A61B 17/105; A61B 90/92
USPC ........... 227/176.1, 175.1, 180.1, 19; 206/340
See application file for complete search history.

(56) References Cited

U.S. PATENT DOCUMENTS

| | | |
|---|---|---|
| 3,017,637 A | 1/1962 | Sampson |
| 3,079,606 A | 3/1963 | Bobrov et al. |
| 3,490,675 A | 1/1970 | Green et al. |
| 3,499,591 A | 3/1970 | Green |
| 4,244,372 A | 1/1981 | Kapitanov et al. |
| 4,344,531 A | 8/1982 | Giersch |
| 4,429,695 A | 2/1984 | Green |
| 4,520,817 A | 6/1985 | Green |
| 4,576,167 A | 3/1986 | Noiles |

(Continued)

FOREIGN PATENT DOCUMENTS

| | | |
|---|---|---|
| AU | 2011250821 A1 | 6/2012 |
| DE | 4300307 A1 | 7/1994 |

(Continued)

OTHER PUBLICATIONS

Australian Patent Examination Report No. 1, dated Oct. 11, 2016, corresponding to Australian Application No. 2013201135; 3 pages.

(Continued)

*Primary Examiner* — Nathaniel Chukwurah

(57) ABSTRACT

A travel clip is provided for use with a surgical staple cartridge. The travel clip includes a cover having first and second side edges which varying in distance from a centerline of the cover and a longitudinally extending rib projecting perpendicularly along the centerline of the cover. The first and second side edges include areas of maximum distance from the centerline of the cover and areas of minimum distance from the centerline of the cover. The space between adjacent areas of maximum distance from the centerline of the cover provide cutouts or openings for viewing, inspection and verification of structure retained within the surgical staple cartridge.

20 Claims, 5 Drawing Sheets

(56) References Cited

U.S. PATENT DOCUMENTS

| | | |
|---|---|---|
| 4,589,413 A | 5/1986 | Malyshev et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,664,305 A | 5/1987 | Blake, III et al. |
| 4,672,964 A | 6/1987 | Dee et al. |
| 4,715,520 A | 12/1987 | Roehr, Jr. et al. |
| 4,763,669 A | 8/1988 | Jaeger |
| 4,819,853 A | 4/1989 | Green |
| 4,863,088 A | 9/1989 | Redmond et al. |
| 4,880,015 A | 11/1989 | Nierman |
| 4,881,544 A | 11/1989 | Green et al. |
| 4,892,244 A | 1/1990 | Fox et al. |
| 4,924,864 A | 5/1990 | Danzig |
| 4,978,049 A | 12/1990 | Green |
| 4,991,764 A | 2/1991 | Mericle |
| 5,014,899 A | 5/1991 | Presty et al. |
| 5,040,715 A | 8/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,083,695 A | 1/1992 | Foslien et al. |
| 5,104,025 A | 4/1992 | Main et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,152,279 A | 10/1992 | Wilk |
| 5,156,315 A | 10/1992 | Green et al. |
| 5,180,092 A | 1/1993 | Crainich |
| 5,209,747 A | 5/1993 | Knoepfler |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,358,506 A | 10/1994 | Green et al. |
| 5,366,133 A | 11/1994 | Geiste |
| 5,366,477 A | 11/1994 | LeMarie, III et al. |
| 5,374,277 A | 12/1994 | Hassler |
| 5,376,095 A | 12/1994 | Ortiz |
| 5,379,933 A | 1/1995 | Green et al. |
| 5,383,888 A | 1/1995 | Zvenyatsky et al. |
| 5,389,098 A | 2/1995 | Tsuruta et al. |
| 5,397,046 A | 3/1995 | Savage et al. |
| 5,397,324 A | 3/1995 | Carroll et al. |
| 5,403,312 A | 4/1995 | Yates et al. |
| 5,413,268 A | 5/1995 | Green et al. |
| 5,415,334 A | 5/1995 | Williamson et al. |
| 5,415,335 A | 5/1995 | Knodell, Jr. |
| 5,423,471 A | 6/1995 | Mastri et al. |
| 5,433,721 A | 7/1995 | Hooven et al. |
| 5,452,837 A | 9/1995 | Williamson, IV et al. |
| 5,465,895 A | 11/1995 | Knodel et al. |
| 5,467,911 A | 11/1995 | Tsuruta et al. |
| 5,470,008 A | 11/1995 | Rodak |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,535,935 A | 7/1996 | Vidal et al. |
| 5,551,622 A | 9/1996 | Yoon |
| 5,562,241 A | 10/1996 | Knodel et al. |
| 5,582,617 A | 12/1996 | Klieman et al. |
| 5,597,107 A | 1/1997 | Knodel et al. |
| 5,601,573 A | 2/1997 | Fogelberg et al. |
| 5,605,272 A | 2/1997 | Witt et al. |
| 5,630,539 A | 5/1997 | Plyley et al. |
| 5,634,584 A | 6/1997 | Okorocha et al. |
| 5,651,491 A | 7/1997 | Heaton et al. |
| 5,653,373 A | 8/1997 | Green et al. |
| 5,655,698 A | 8/1997 | Yoon |
| 5,662,258 A | 9/1997 | Knodel et al. |
| 5,662,259 A | 9/1997 | Yoon |
| 5,662,260 A | 9/1997 | Yoon |
| 5,673,841 A | 10/1997 | Schulze et al. |
| 5,680,982 A | 10/1997 | Schulze et al. |
| 5,681,330 A | 10/1997 | Hughett et al. |
| 5,715,988 A | 2/1998 | Palmer |
| 5,718,359 A | 2/1998 | Palmer et al. |
| 5,762,255 A | 6/1998 | Chrisman et al. |
| 5,794,834 A | 8/1998 | Hamblin et al. |
| 5,797,537 A | 8/1998 | Oberlin et al. |
| 5,800,449 A | 9/1998 | Wales |
| 5,816,471 A | 10/1998 | Plyley et al. |
| 5,820,009 A | 10/1998 | Melling et al. |
| 5,893,506 A | 4/1999 | Powell |
| 5,901,895 A | 5/1999 | Heaton et al. |
| 5,911,352 A | 6/1999 | Racenet et al. |
| 5,984,938 A | 11/1999 | Yoon |
| 5,988,479 A | 11/1999 | Palmer |
| 5,993,465 A | 11/1999 | Shipp et al. |
| 6,010,054 A | 1/2000 | Johnson et al. |
| 6,032,849 A | 3/2000 | Mastri et al. |
| 6,050,472 A | 4/2000 | Shibata |
| 6,079,606 A | 6/2000 | Milliman et al. |
| 6,109,500 A | 8/2000 | Alli et al. |
| 6,119,913 A | 9/2000 | Adams et al. |
| 6,131,789 A | 10/2000 | Schulze et al. |
| 6,174,309 B1 | 1/2001 | Wrublewski et al. |
| 6,241,139 B1 | 6/2001 | Milliman et al. |
| 6,241,140 B1 | 6/2001 | Adams et al. |
| 6,601,749 B2 | 8/2003 | Sullivan et al. |
| 6,607,540 B1 | 8/2003 | Shipp |
| 6,755,338 B2 | 6/2004 | Hahnen et al. |
| 6,805,273 B2 | 10/2004 | Bilotti et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,055,731 B2 | 6/2006 | Shelton, IV et al. |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,278,563 B1 | 10/2007 | Green |
| RE40,237 E | 4/2008 | Bilotti et al. |
| 7,380,696 B2 | 6/2008 | Shelton, IV et al. |
| 7,407,078 B2 | 8/2008 | Shelton, IV et al. |
| 7,434,717 B2 | 10/2008 | Shelton, IV et al. |
| 7,451,904 B2 | 11/2008 | Shelton, IV |
| 7,464,849 B2 | 12/2008 | Shelton, IV et al. |
| 7,503,474 B2 | 3/2009 | Hillstead et al. |
| 7,568,604 B2 | 8/2009 | Ehrenfels et al. |
| 7,631,794 B2 | 12/2009 | Rethy et al. |
| 9,113,881 B2 | 8/2015 | Scirica |
| 2004/0007608 A1* | 1/2004 | Ehrenfels ......... A61B 17/07207 227/176.1 |
| 2005/0070758 A1 | 3/2005 | Wells et al. |
| 2005/0139636 A1 | 6/2005 | Schwemberger et al. |
| 2005/0145672 A1 | 7/2005 | Schwemberger et al. |
| 2005/0184124 A1 | 8/2005 | Scirica et al. |
| 2005/0222616 A1 | 10/2005 | Rethy et al. |
| 2005/0247752 A1 | 11/2005 | Kelly et al. |
| 2005/0247753 A1 | 11/2005 | Kelly et al. |
| 2006/0144898 A1 | 7/2006 | Bilotti et al. |
| 2006/0226195 A1 | 10/2006 | Scirica et al. |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0114261 A1 | 5/2007 | Ortiz et al. |

(56) References Cited

U.S. PATENT DOCUMENTS

| | | |
|---|---|---|
| 2007/0175950 A1 | 8/2007 | Shelton et al. |
| 2007/0181631 A1 | 8/2007 | Bilotti et al. |
| 2007/0219563 A1 | 9/2007 | Voegele |
| 2007/0221702 A1 | 9/2007 | Kruszynski |
| 2007/0246508 A1 | 10/2007 | Green |
| 2007/0255296 A1 | 11/2007 | Sauer |
| 2008/0027466 A1 | 1/2008 | Vitali et al. |
| 2008/0093415 A1 | 4/2008 | Bilotti |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0272171 A1 | 11/2008 | Viola |
| 2008/0302854 A1 | 12/2008 | Rethy et al. |
| 2009/0008424 A1 | 1/2009 | Green |
| 2009/0134199 A1 | 5/2009 | Heinrich et al. |
| 2009/0206131 A1 | 8/2009 | Weisenburgh, II et al. |
| 2009/0272784 A1 | 11/2009 | Farascioni |
| 2011/0101066 A1 | 5/2011 | Farascioni et al. |

FOREIGN PATENT DOCUMENTS

| | | |
|---|---|---|
| EP | 0484677 A1 | 5/1992 |
| EP | 0537498 A2 | 4/1993 |
| EP | 0589306 A2 | 3/1994 |
| EP | 0591946 A1 | 4/1994 |
| EP | 0592243 A2 | 4/1994 |
| EP | 0600182 A2 | 6/1994 |
| EP | 0621009 A1 | 10/1994 |
| EP | 0656188 A2 | 6/1995 |
| EP | 1550410 A2 | 7/2005 |
| EP | 1908413 A1 | 4/2008 |
| EP | 2462875 A2 | 6/2012 |
| FR | 2681775 A1 | 4/1993 |
| WO | 03022133 A2 | 3/2003 |
| WO | 03079909 A2 | 10/2003 |

OTHER PUBLICATIONS

European Search Report dated Oct. 5, 2015, corresopnding to European Application No. 13159351.9; 7 pages.
European Search Report for EP 10251882.6-1269 date of completion is Feb. 17, 2011 (3 pages).
European Search Report for EP 11178544 dated Sep. 29, 2011.

* cited by examiner

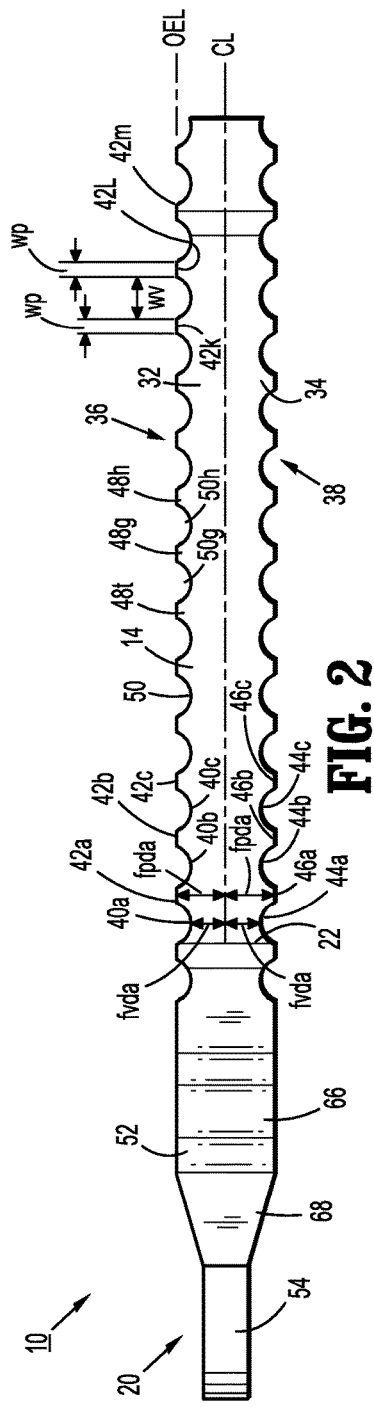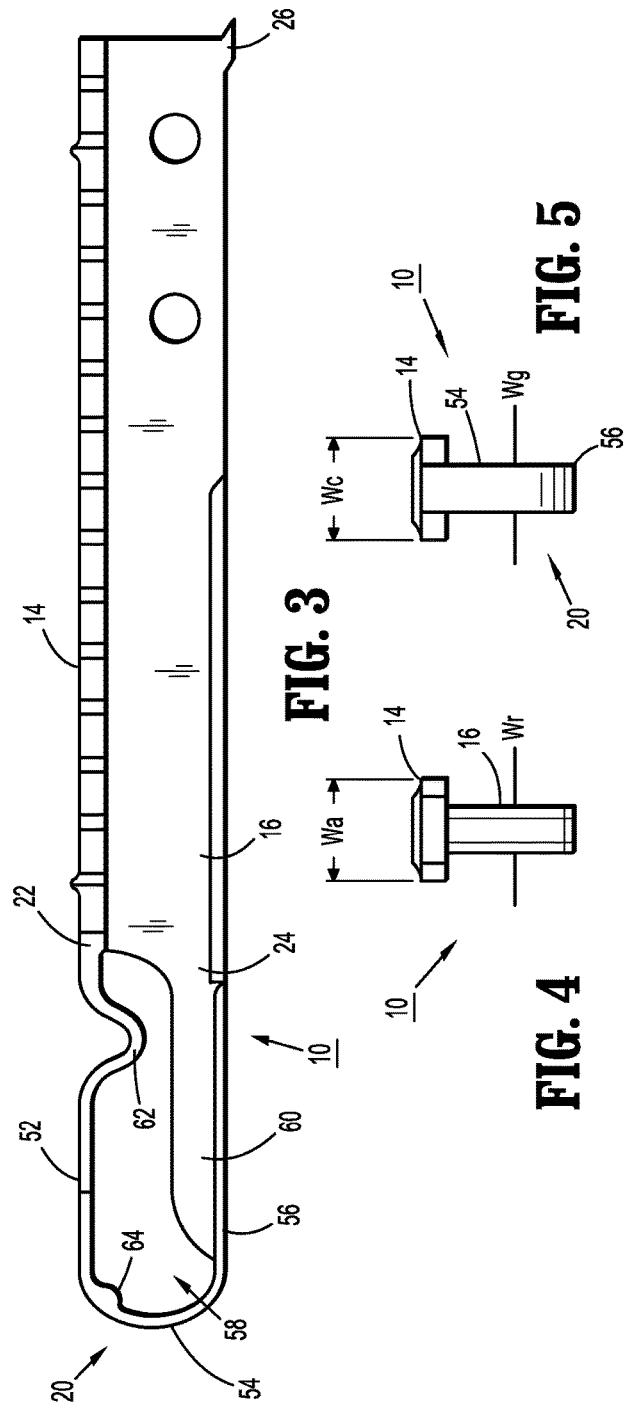

TRAVEL CLIP FOR SURGICAL STAPLE CARTRIDGE

CROSS-REFERENCE TO RELATED APPLICATION(S)

This application is a Divisional application of U.S. patent application Ser. No. 13/422,320, filed on Mar. 16, 2012, the entire contents of which are incorporated by reference herein.

BACKGROUND

1. Technical Field

The present disclosure relates to a travel clip or shipping aid for use with a surgical staple cartridge. More particularly, the present disclosure relates to a removable travel clip for retaining components within a staple cartridge while allowing viewing of those components for inspection and verification of type.

2. Background of Related Art

Certain surgical procedures often require forming lines of staples through tissue sections and, in some instances, severing the tissue between the staple lines with a knife blade. Surgical staplers typically include a removable staple containing cartridge for use with a surgical stapler. The removable staple cartridge generally includes an outer support or frame member and a body portion containing one or more rows of staple containing pockets. In some cases, the staple cartridge includes a plurality of longitudinally staggered rows of staple containing pockets.

The staple containing pockets formed in the cartridge are open to a tissue engaging surface on the top of the insert and extend through openings in the bottom. The staple containing pockets each contain a surgical staple adjacent the tissue engaging surface of the cartridge and a pusher positioned beneath the surgical staple for driving the surgical staple out of the staple cartridge.

Often during shipment and assembly, the staple cartridge is shipped separately from the outer support or frame member. In these instances, the bottom of the staple cartridge is open and/or uncovered risking loss of the pushers loosely contained within the staple pockets. In other instances, a cover is used that completely obscures the tissue engaging surface of the staple cartridge.

Additionally, bottom surfaces of the pushers are often marked with various indicia to indicate the size and/or type of the surgical staples contained within the staple cartridge. This facilitates inspection and verification of the contents of the staple cartridge and speeds up the assembly process of the final staple cartridge. However, if a cover is utilized to retain the pushers within the staple pockets, the indicia on the bases of the pushers cannot be inspected without removing the cover.

Therefore, a need exists for a travel clip or shipping aid for retaining the pushers within the staple pockets. A further need exists for a travel clip or shipping aid for retaining pushers within staple pockets while allowing for inspection of the bases of the pushers. A need exists for identification of the cartridge and indication of the presence of the staples and pushers.

SUMMARY

There is disclosed a travel clip for use with a surgical staple cartridge. The travel clip generally includes a longitudinally extending cover having a first side having a first edge, a second side having a second edge, a distal end, a proximal end; and a longitudinal rib projecting perpendicularly from an underside of the cover. The rib extends along a centerline of the cover. The first edge of the first side has a varying distance from the centerline of the cover. Specifically, the first edge has a plurality of areas of maximum distance from the centerline and a plurality of areas of minimum distance from the centerline. The areas of maximum distance from the centerline form posts and the areas of minimum distance from the centerline form valleys. In a particular embodiment, the posts have relatively flat peaks and adjacent posts define cutouts therebetween. In one embodiment the cutouts are semi-circular and relatively flat peaks are parallel to the centerline.

There is also disclosed a travel clip for use with a surgical staple cartridge including a longitudinally extending cover having a first side having a first edge, a second side having a second edge, a distal end and a proximal end. A longitudinal rib projects perpendicularly from an underside of the cover. The first edge of the first side has a varying distance from a centerline of the cover and the second edge of the second side has a varying distance from the centerline of the cover.

The first edge includes first posts separated by first cutouts intermediate the first posts and the second edge includes second posts separated by second cutouts intermediate the second posts. In a specific embodiment, the first posts on the first edge are directly opposite the second posts on the second edge.

In a more specific embodiment, the first posts have relatively flat first peaks and the second posts have relatively flat second peaks. The relatively flat first peaks are parallel to the relatively flat second peaks.

There is further disclosed a travel clip for use with a surgical staple cartridge including a longitudinally extending cover having a first side having a first edge, a second side having a second edge, a distal end and a proximal end. The first edge of the first side has a varying distance from a centerline of the cover and the second edge of the second side has varying distance from the centerline of the cover. A longitudinal rib projects perpendicularly from an underside of the cover. In this embodiment, a grasping structure extends from proximal ends of the cover and rib to facilitate manipulation of the travel clip.

The grasping structure generally includes an upper portion extending proximally from a proximal end of the cover, a proximal portion and a lower portion extending proximally from a proximal end of the rib. In a specific embodiment, the upper portion includes a wider distal portion and a narrower proximal portion. The travel clip further includes a rib extension extending proximally from a proximal end of the rib and over the lower portion of the grasping structure.

The travel clip may also include a distally extending tooth projecting from a distal end of the rib to facilitate insertion of the travel clip into a staple cartridge.

DESCRIPTION OF THE DRAWINGS

An embodiment of the presently disclosed travel clip for use with a surgical staple cartridge is disclosed herein with reference to the drawings, wherein:

FIG. 2 is a top view of the travel clip;

FIG. 3 is a side view of the travel clip;

FIG. 4 is a front end view of the travel clip;

FIG. 5 is a rear end view of the travel clip;

DETAILED DESCRIPTION OF EMBODIMENTS

An embodiment of the presently disclosed travel clip for use with a surgical staple cartridge will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
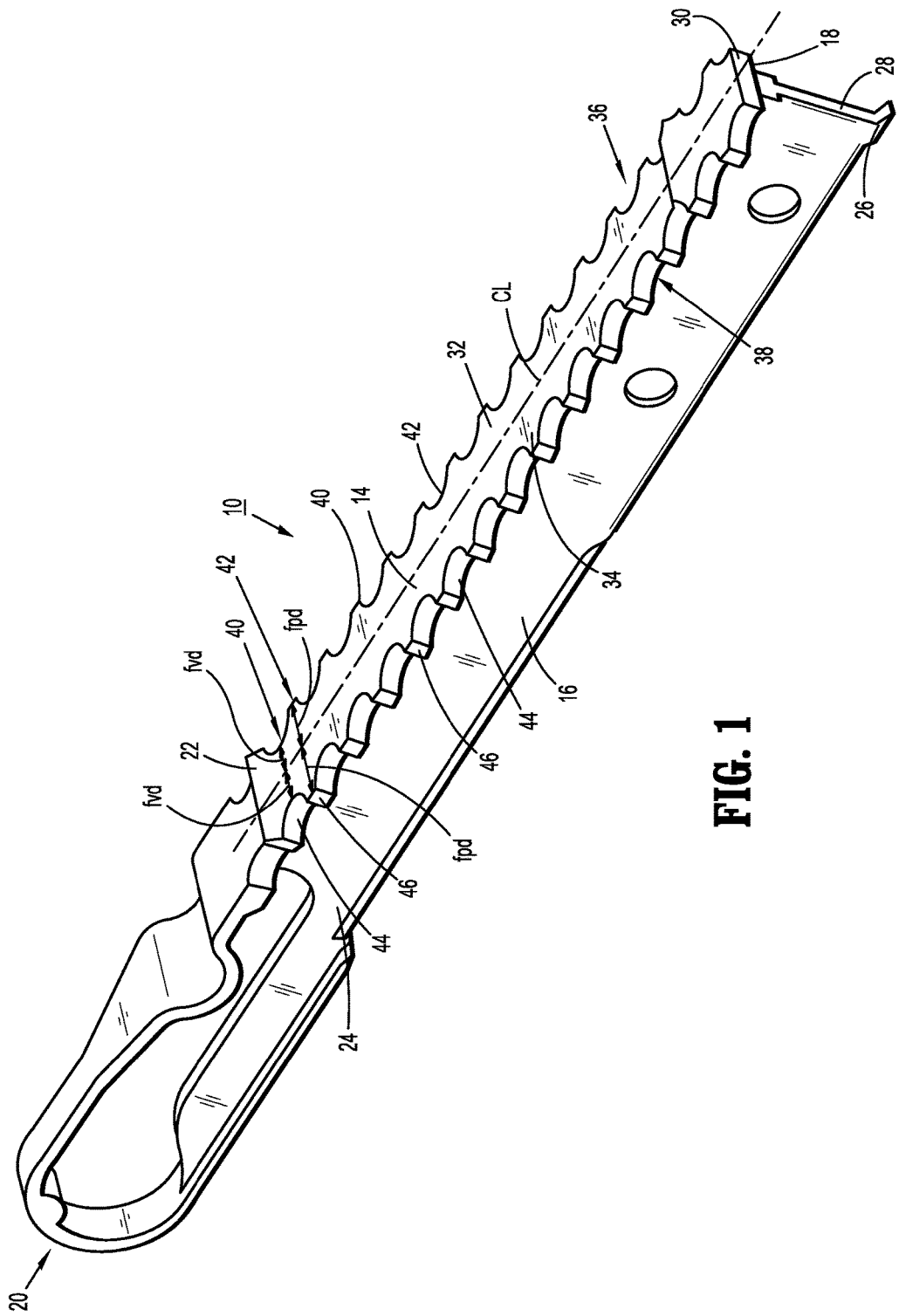
FIG. 1 is a perspective view of an embodiment of a travel clip for use with a surgical staple cartridge.
Figure 6:
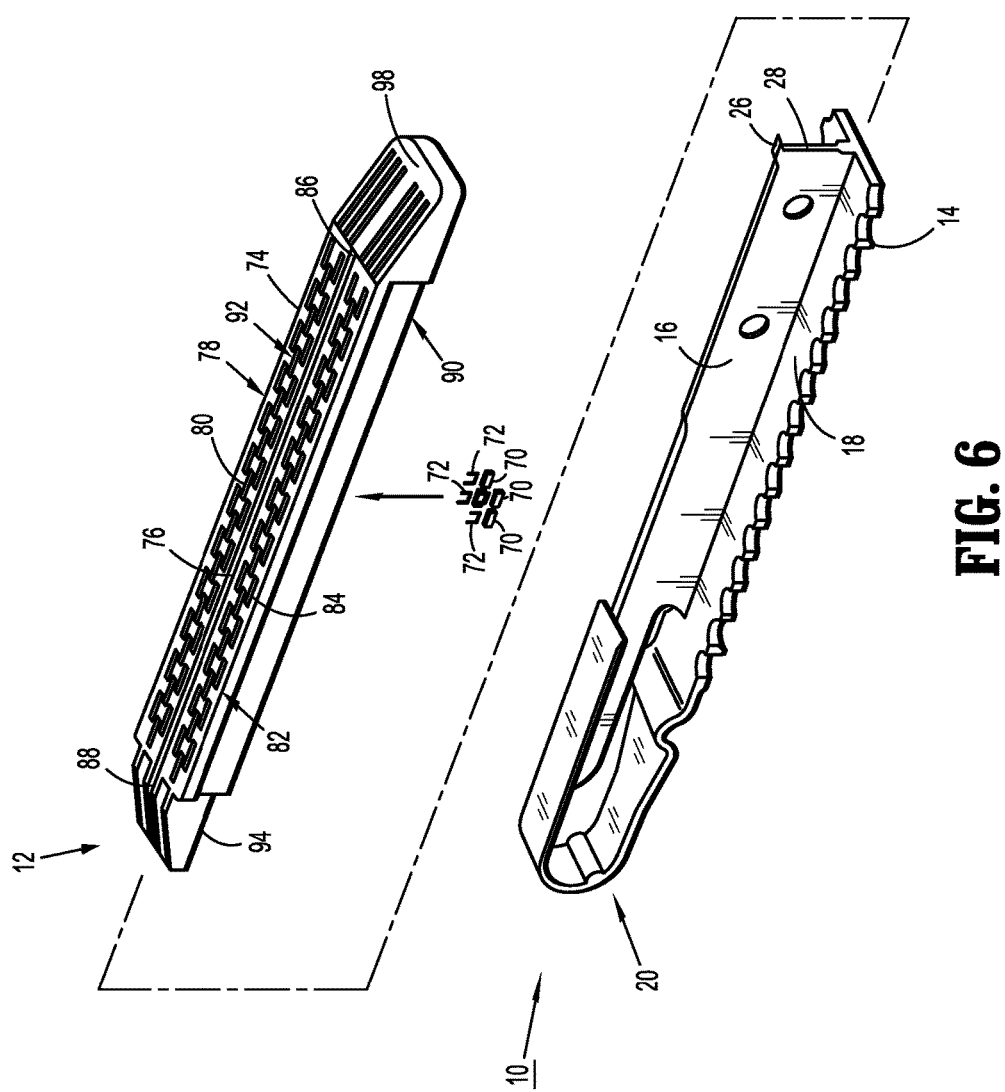
FIG. 6 is a perspective view, with parts separated, of the travel clip and a staple cartridge and associated surgical staples and staple pushers.

Referring initially to FIG. 1, there is disclosed a travel clip 10 for use with a staple cartridge 12 (FIG. 6). Travel clip 10 is provided to secure various components contained within staple cartridge 12 while allowing the components to be viewed for inspection during various stages of assembly of a final staple cartridge. Travel clip 10 may be formed from a variety of materials, including thermoplastics, metallic materials, etc. Additionally, travel clip may be color coded to reflect the contents of staple cartridge 12.

Travel clip 10 generally includes an elongate, rectangular base or cover 14 and a longitudinally extending rib 16 extending from an underside 18 of cover 14. Gripping structure 20 extends from proximal ends 22 and 24 of cover 14 and rib 16, respectively, and facilitates manipulating travel clip 10 relative to staple cartridge 12. A distally extending tooth 26 extends from a distal end 28 of rib 16 to guide travel clip 10 onto staple cartridge 12 in a manner described in more detail hereinbelow.

Referring to FIGS. 1 and 2, cover 14 includes a distal end 30, proximal end 22 and first and second sides 32 and 34. First and second sides 32 and 34 extend outwardly from a center line CL of cover 14 and include first and second side edges 36 and 38, respectively. In order to view structure contained within staple cartridge 12 located beneath cover 14, first and second side edges 36 and 38 are not completely linear but each varies in distance from center line CL to expose underlying structure. For example, in this embodiment, first side edge 36 varies in distance from centerline CL from points or first valleys 40 of minimum distance fvd from centerline CL outward to points or first peaks 42 of maximum distance fpd from centerline CL and extending along first side edge 36. As best shown in FIG. 2, first side 32 includes a plurality of first valleys 40a, 40b, 40c . . . etc., separated by first peaks 42a, 42b, 42c . . . etc.

Similarly, second side edge 38 also varies in distance from centerline CL from points or second valleys 44 of minimum distance svd from centerline CL outward to points or peaks 46 of maximum distance spd from centerline CL and extending along second side edge 38.

Referring now specifically to FIG. 2, second side 34 also includes a plurality of second valleys 44a, 44b, 44c . . . etc. separated by second peaks 46a, 46b, 46c . . . etc. In this embodiment, second side 34 is a mirror image of first side 32. While the following discussion is given with respect to the details of first side 32, it will be appreciated that second side 34 is configured similarly.

The areas of cover 14 located between first valleys 40 of minimum distance fvd from centerline CL form first posts 48, such as first posts 48f, 48g, 48h . . . etc defining openings or cutouts 50g, 50h . . . etc. between adjacent posts 48f, 48g, . . . etc for viewing of underlying structure. As shown, in this disclosed embodiment, a width wp of peaks 42, for example, peaks 42k, 42L, 42m . . . etc, is constant and is less than the width wv between adjacent peaks 42k and 42L, etc. This provides sufficient surface area of posts 48 to retain underlying structure while allowing viewing of the underlying structure through cutouts 50. As shown, peaks 42 are relatively flat and equidistant from centerline CL and extend along an outer edge line OEL parallel to centerline CL.

It should be noted that, while in this particular embodiment, first side 32 is illustrated with generally flat first peaks 42 and semi-cylindrical cutouts 50, first side 32 may assume other shapes including rounded peaks, sharp v-shaped valleys, etc. First side edge 36 may also have different configurations, such as, for example, sinusoidal, etc. Also, distances fpda, fpdb, etc. between various peaks 42a, 42b . . . etc and centerline CL need not be constant but may vary between themselves as well as having variable distances fvda, fvdb . . . etc. from first valleys 40a, 40b, etc. to centerline CL. Further, widths wp of first peaks 42 may also vary along first side edge 36 as well as widths wv of first valleys 40.

Referring to FIG. 3, grasping structure 20 generally includes an upper portion 52 extending from proximal end 22 of cover 14, a rounded proximal portion 54 and a lower portion 56 extending from proximal end 24 of rib 16. Upper portion 52, proximal portion 54 and lower portion 56 are formed of a relatively flexible material and together define an opening 58 through which a user may insert a finger to better pull travel clip 10 off staple cartridge 12. A rib extension 60 extends proximally from proximal end 24 of rib 16 serves to stiffen lower portion 56. Upper portion 52 includes a dip 62 adjacent proximal end 22 of cover 14 which provides a tactile indication of a user's finger position on travel clip 10 as well as increasing the flexibility of upper portion 52. A nub 64 projects inwardly from proximal portion 54 and into opening 58 to provide stiffness between upper portion 52 and proximal portion 54. As best shown in FIG. 2, upper portion 52 includes a constant width distal portion 66 extending from cover 14 and a proximal tapered portion 68 connected to proximal portion 54 of grasping structure 20.

With reference to FIGS. 4 and 5, it can be seen that cover 14 has an overall width We greater that width Wr of rib 16 (FIG. 4) and width Wg of proximal portion 54 and lower portion 56 of grasping structure 20 (FIG. 5).

Turning now to FIG. 6, staple cartridge 12 generally includes a plurality of pushers 70 and surgical staples 72 which are movably retained in a staple cartridge body 74. Staple cartridge body 74 includes a longitudinally extending knife slot 76. First longitudinally extending rows 78 of openings or staple pockets 80 and second longitudinally extending rows 82 of openings or staple pockets 84 are situated on opposed sides of knife slot 76. Knife slot 76 terminates in a closed distal end 86 within staple cartridge body 74 and has an open proximal end 88 for receipt of a knife (not shown) associated with a surgical stapling instrument (not shown) as well as receiving rib 16 of travel clip 10 as described hereinbelow. Staple pockets 80 and 84 extend completely through staple cartridge body 74 and extend from a bottom surface 90 of staple cartridge body 74 to a tissue engaging upper surface 82 of staple cartridge body 74. Surgical staples 72 are frictionally retained within staple pockets 80 and 84 and are positioned slightly below tissue engaging surface 92 of staple cartridge body 74. Pushers 70 are located within staple pockets 80 and 84 beneath surgical staples 72 and are free to move within staple pockets 80 and 84.

Figure 7:
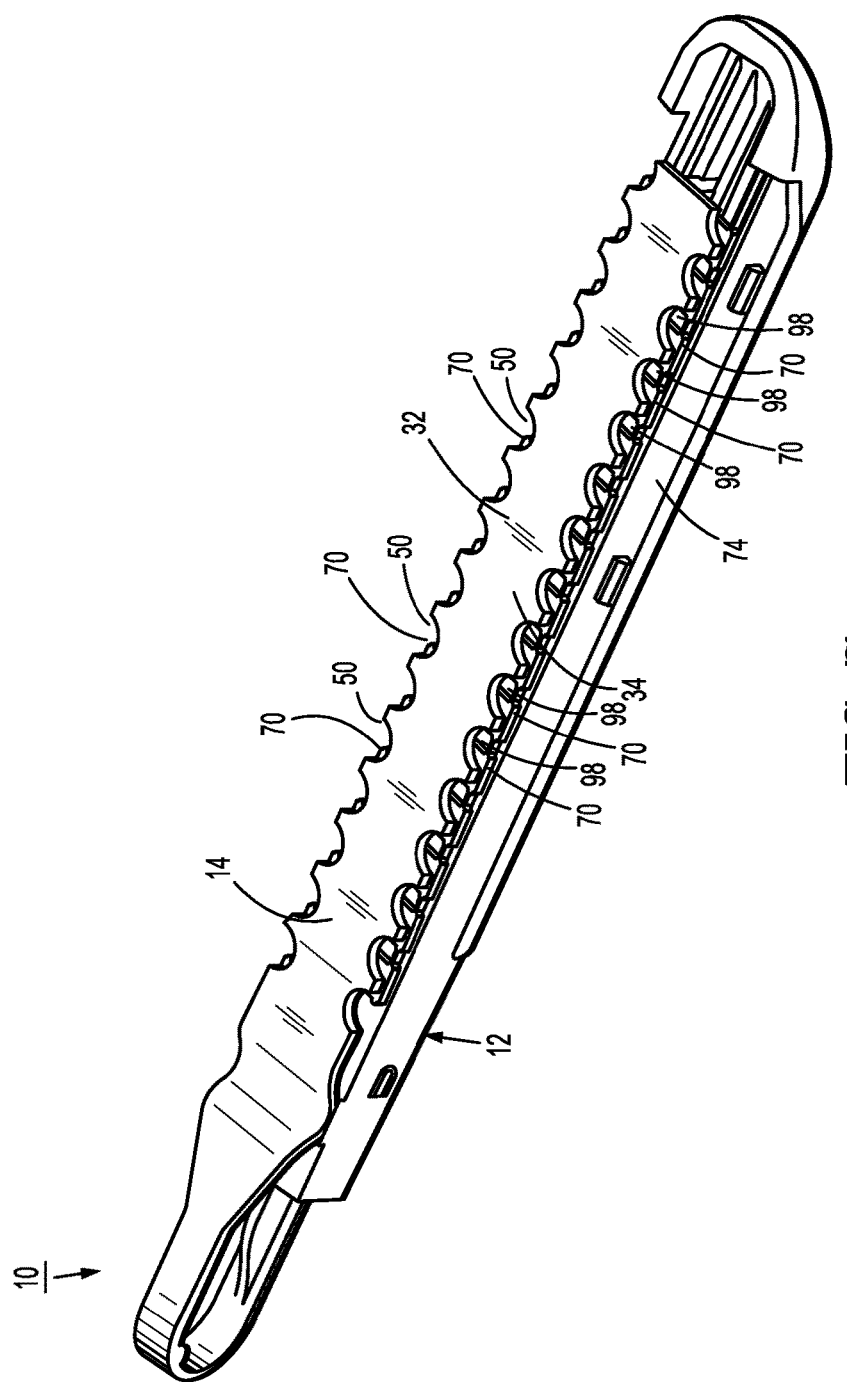
FIG. 7 is a perspective view of the travel clip assembled on the staple cartridge.

Referring now to FIGS. 6-9, and initially with regard to FIG. 6, the use of travel clip 10 to retain pushers 70 within staple cartridge body 74 for transportation and inspection will now be described. Initially, staple cartridge 12 is assembled with surgical staples 72 and pushers 70 positioned within staple pockets 80 and 84. Travel clip 10 is held at grasping structure 20 and distal end 28 of rib 16 is inserted into proximal end 88 of knife slot 78. As noted hereinabove, tooth 26 on distal end 28 of rib 16 facilitates insertion of rib 16 into knife slot 76. The tooth also engages the distal end of the cartridge to keep the clip located properly. Travel clip 10 is advanced distally through staple cartridge body 74 from a proximal end 94 of staple cartridge body 74 toward an angled distal end 96 of staple cartridge body 74. Rib 16 is advanced through knife slot 76 until distal end 28 of rib 16 abuts closed distal end 86 of knife slot 74. At this point, underside 18 of travel clip 10 is positioned over bottom surface 90 of staple cartridge body 74 as best shown in FIG. 7.

Referring to FIG. 7, it can be seen that when travel clip 10 is fully inserted through staple cartridge body 74, pushers 70, contained within staple pockets 80 and 84 are visible through cutouts 50 in first side 32 of cover 14 and cutouts 98 formed in second side 34 of cover 14. This allows a user to inspect pushers 70 to ensure the presence of the pushers, and for proper positioning, and to determine any indicia or coloration that indicate the size and/or type of surgical staples 72 contained within staple cartridge body 74.

Figure 8:
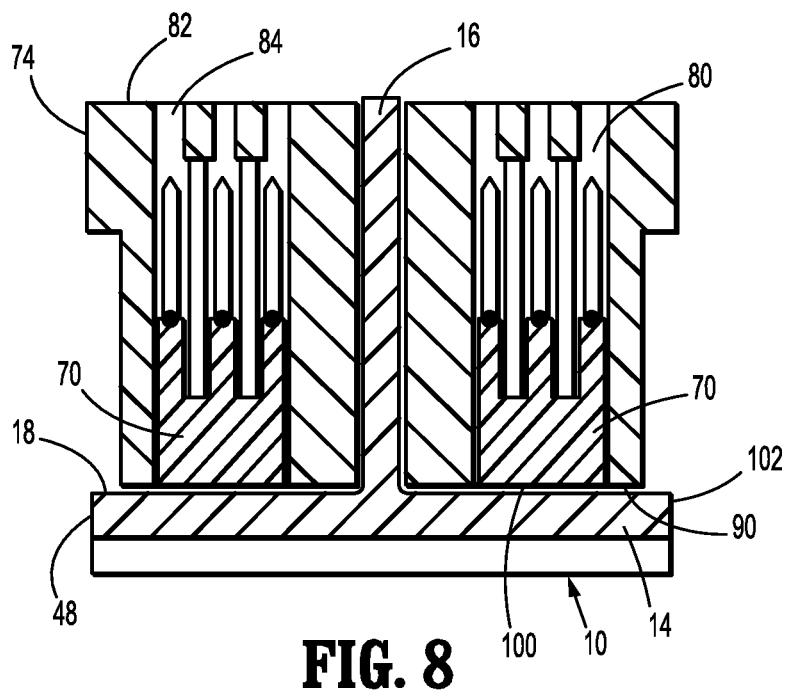
FIG. 8 is a cross-sectional view of the travel clip assembled on the staple cartridge.
Figure 9:
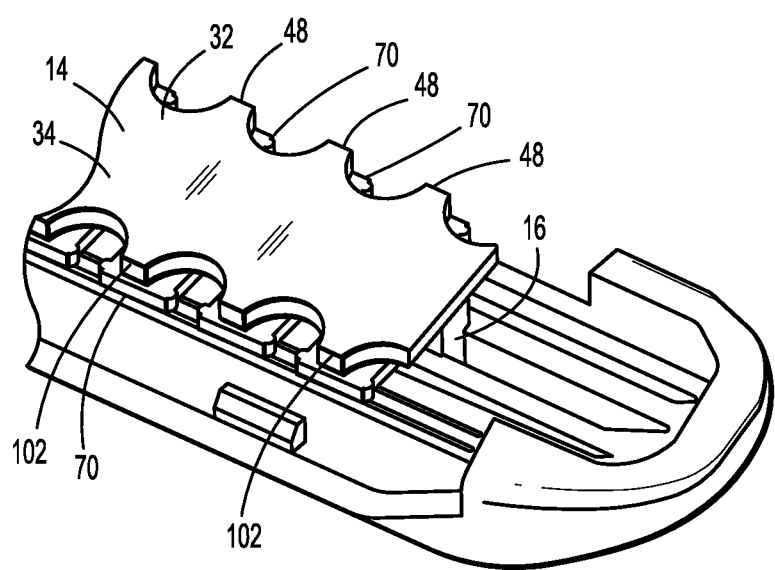
FIG. 9 is an enlarged perspective view of the distal end of the assembled travel clip and staple cartridge.

Referring now to FIGS. 7-9, in addition to allowing pushers 70 to be visible, cover 14 of travel clip 10 retains pushers within staple pockets 80 and 84 during shipping and inspection. With specific reference to FIG. 8, underside 18 of cover 14 engages bases 100 of pushers 70 located within staple pockets 80 and 84 to prevent pushers 70 and surgical staples 72 from falling out of staple cartridge body 74. Specifically, first posts 48 formed in first side 32 of cover 14 retain pushers 70 within second rows 82 of staple pockets 84 while second posts 102 formed in second side 38 of cover 14 retain pushers 70 within first rows 78 of staple pockets 80. Thus, travel clip 10 provides a way of securing pushers 70 within staple pockets 80 and 84 in staple cartridge body 74 while allowing pushers 70 to be visible for inspection.

It will be understood that various modifications may be made to the embodiments disclosed herein. For example, cutout may be provided on only one side of the cover of the disclosed travel clip. Further, cutouts need not be provided above each pusher but may be located above alternate staple pockets or randomly. Additionally, the viewing areas of the cover of the disclosed travel clip may include other variations in the sides of the cover edges, such as, for example, sinusoidal, posts with sharp or rounded peaks rather than flat, and other shapes for the cutouts, such as, for example, semi-oval, square, rectangular, etc. Therefore, the above description should not be construed as limiting, but merely as exemplifications of particular embodiments. Those skilled in the art will envision other modifications within the scope and spirit of the claims appended hereto.

The invention claimed is:

1. A travel clip for use with a surgical staple cartridge comprising:
    a longitudinally extending cover configured to be positioned on a bottom surface of a surgical staple cartridge, the cover defining at least one opening therethrough for viewing internal structure of a surgical staple cartridge;
    a longitudinal rib projecting from an underside of the cover and configured for receipt in a knife slot of a surgical staple cartridge; and
    a grasping structure extending from at least one of a proximal end of the cover or a proximal end of the rib.

2. The travel clip as recited in claim 1, wherein the cover includes:
    a first side having a first edge; and
    a second side having a second edge, wherein at least one of the first edge or the second edge has a plurality of areas of maximum distance from a centerline of the cover, and a plurality of areas of minimum distance from the centerline.

3. The travel clip as recited in claim 2, wherein the areas of maximum distance from the centerline form posts.

4. The travel clip as recited in claim 3, wherein the posts have flat peaks.

5. The travel clip as recited in claim 4, wherein the flat peaks are parallel to the centerline.

6. The travel clip as recited in claim 3, wherein the at least one opening is disposed between adjacent posts.

7. The travel clip as recited in claim 6, wherein the at least one opening is semi-circular.

8. The travel clip as recited in claim 2, wherein the areas of minimum distance from the centerline form valleys.

9. The travel clip as recited in claim 1, wherein the proximal end of the longitudinal rib is disposed adjacent the proximal end of the cover, and wherein the rib has a distal end disposed adjacent a distal end of the cover such that the rib extends along a centerline of the cover.

10. The travel clip as recited in claim 1, wherein the grasping structure includes:
    an upper portion extending proximally from the proximal end of the cover;
    a lower portion extending proximally from the proximal end of the rib; and
    a rounded proximal portion interconnecting the upper portion and the lower portion to define an opening.

11. The travel clip as recited in claim 10, wherein the upper portion tapers from a distal portion of the upper portion to a proximal portion of the upper portion.

12. The travel clip as recited in claim 10, further comprising a rib extension extending proximally from the proximal end of the rib, and wherein the rib extension is disposed within the opening of the grasping structure and in engagement with the lower portion of the grasping structure.

13. The travel clip as recited in claim 1, further comprising a distally extending tooth projecting from a distal end of the rib.

14. A travel clip for use with a surgical staple cartridge comprising:
    a longitudinally extending cover defining at least one opening therethrough for viewing structure under the cover;
    a longitudinal rib projecting from an underside of the cover, wherein the underside of the cover is configured to engage bottom portions of pushers disposed adjacent a bottom surface of a surgical staple cartridge to retain the pushers therein; and
    a grasping structure extending from at least one of a proximal end of the cover or a proximal end of the longitudinal rib.

15. The travel clip as recited in claim 14, wherein the cover includes:

a first side having a first edge; and a second side having a second edge, wherein at least one of the first edge or the second edge has a plurality of areas of maximum distance from a centerline of the cover, and a plurality of areas of minimum distance from the centerline.

16. The travel clip as recited in claim 14, wherein the grasping structure includes:

an upper portion extending proximally from the proximal end of the cover;

a lower portion extending proximally from the proximal end of the longitudinal rib; and a rounded proximal portion interconnecting the upper portion and the lower portion to define an opening.

17. The travel clip as recited in claim 16, further comprising a rib extension extending proximally from the proximal end of the rib, the rib extension disposed within the opening of the grasping structure and in engagement with the lower portion of the grasping structure.

18. The travel clip as recited in claim 14, wherein the proximal end of the rib is disposed adjacent the proximal end of the cover, and wherein the rib has a distal end disposed adjacent a distal end of the cover such that the rib extends along a centerline of the cover.

19. A travel clip for use with a surgical staple cartridge comprising:

a longitudinally extending cover configured to be positioned on a surgical staple cartridge;

a longitudinal rib projecting from an underside of the cover and configured for receipt in a knife slot of a surgical staple cartridge, wherein the rib extends along a majority of a length of the cover; and a grasping structure extending from at least one of a proximal end of the cover or a proximal end of the rib.

20. The travel clip as recited in claim 14, wherein the rib extends along a majority of a length of the cover.

* * * * *